US012642928B2

(12) United States Patent
Schregel

(10) Patent No.: US 12,642,928 B2
(45) Date of Patent: Jun. 2, 2026

(54) CONTAMINATION PREVENTION IN THE BLOWER OF A VENTILATOR

(71) Applicant: Loewenstein Medical Technology S.A., Luxembourg (LU)

(72) Inventor: Christian-Georg Schregel, Friedberg (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 796 days.

(21) Appl. No.: 18/056,830

(22) Filed: Nov. 18, 2022

(65) Prior Publication Data

US 2023/0166062 A1 Jun. 1, 2023

(30) Foreign Application Priority Data

Nov. 29, 2021 (DE) .......................... 102021005886.0

(51) Int. Cl.
| | |
|---|---|
| *A61M 16/00* | (2006.01) |
| *A61M 16/01* | (2006.01) |
| *A61M 16/08* | (2006.01) |
| *A61M 16/12* | (2006.01) |
| *F04D 29/10* | (2006.01) |
| *F04D 29/42* | (2006.01) |
| *F04D 29/58* | (2006.01) |

(52) U.S. Cl.
CPC .... *A61M 16/0066* (2013.01); *A61M 16/0875* (2013.01); *F04D 29/104* (2013.01); *F04D 29/4226* (2013.01); *A61M 16/01* (2013.01); *A61M 16/12* (2013.01); *F04D 29/5806* (2013.01)

(58) Field of Classification Search
CPC ............. A61M 16/0066; A61M 16/01; A61M 16/0875; A61M 16/12; A61M 2202/20; A61M 2202/203; A61M 2202/206; F04D 29/102; F04D 29/104; F04D 29/4226; F04D 29/5806
See application file for complete search history.

(56) References Cited

U.S. PATENT DOCUMENTS

| | | | | |
|---|---|---|---|---|
| 2003/0084900 | A1* | 5/2003 | Leclerc ................. | F04D 17/164 |
| | | | | 128/204.18 |
| 2009/0291004 | A1* | 11/2009 | Grasmuck ................ | H02K 5/12 |
| | | | | 417/423.1 |
| 2010/0189554 | A1* | 7/2010 | Grasmuck ................ | H02K 9/14 |
| | | | | 415/198.1 |
| 2011/0288428 | A1* | 11/2011 | Valentine ............... | A61B 5/097 |
| | | | | 128/205.12 |
| 2014/0020684 | A1* | 1/2014 | Klasek .................. | A61M 16/16 |
| | | | | 128/203.26 |
| 2022/0360143 | A1* | 11/2022 | Prat ....................... | A61M 16/12 |

FOREIGN PATENT DOCUMENTS

| | | | | | |
|---|---|---|---|---|---|
| EP | | 3093498 | A1 * | 11/2016 | ......... F04D 29/4206 |
| FR | | 2910081 | A1 | 6/2008 | |
| FR | | 2910078 | B1 | 2/2009 | |
| WO | WO-2017039497 | A1 * | 3/2017 | ........ A61M 16/1005 |

* cited by examiner

*Primary Examiner* — Joseph D. Boecker
(74) *Attorney, Agent, or Firm* — Abel Schillinger, LLP

(57) ABSTRACT

A ventilator having at least one motor-operated blower for generating an air flow. The blower is configured and designed such that during the generation of the air flow in the blower different pressure regions with different pressures are formed in such a way that an air flow in the direction of the motor is prevented.

18 Claims, 4 Drawing Sheets

CONTAMINATION PREVENTION IN THE BLOWER OF A VENTILATOR

CROSS-REFERENCE TO RELATED APPLICATIONS

The present application claims priority under 35 U.S.C. § 119 of German Patent Application No. 102021005886.0, filed Nov. 29, 2021, the entire disclosure of which is expressly incorporated by reference herein.

BACKGROUND OF THE INVENTION

1. Field of the Invention

The present invention relates to the contamination prevention in the blower of a ventilator.

2. Discussion of Background Information

Ventilators, anesthesia appliances and respiratory therapy appliances for ventilation or respiratory assistance or for cough assistance have a blower for generating a respiratory air flow in order to perform respiratory therapy. At least one rotatably mounted fan wheel (also designated as an impeller) with a plurality of blade elements is usually arranged in the housing of the blower and is driven by a motor.

Particularly when operating a blower in the context of a semi-closed circuit, as is the case in anesthesia appliances for example, the respiratory air from the patient may result in microbial contamination even at locations that are difficult to reach, e.g., on the drive shaft or in the motor bearing of the blower.

When treating blowers in cleaning and disinfecting equipment, two basic problems arise. The first problem is the effect that the cleaning and disinfecting has on the motor. In the motor, contact with the generally chemically aggressive cleaning liquids leads, among other things, to wear at the bearings and at bonding points or, in the case of unfavorable pairings of materials, to contact corrosion. The second problem is the poor cleaning achieved at the locations that are difficult to reach. Compared to the directly accessible parts such as the fan wheel or the fan wheel housing, the cleaning liquid can pass only indirectly into the spaces at the locations that are difficult to reach, and this reduces the impact energy of the liquid and potentially also entails a drop in temperature.

Purely mechanical sealing of the fan wheel housing in order to avoid penetration of microbes is disadvantageous in intensive care ventilation and anesthesia, since blowers used in these situations have to be operated at very high speeds (50,000-100,000 rpm), and fully sealed bearings are associated with higher frictional losses.

In view of the foregoing, it would be advantageous to have available an efficient, long-life ventilator that can be operated free of microbes.

SUMMARY OF THE INVENTION

The invention provides a ventilator having at least one motor-operated blower for generating an air flow. According to the invention, the blower is configured and designed such that, during the generation of the air flow in the blower, different pressure regions with different pressures are formed in such a way that an air flow in the direction of the motor is prevented.

In some embodiments, the ventilator is characterized in that the blower comprises at least one motor part with the motor and a drive shaft and also a blower head with a rotatably mounted fan wheel, wherein, between the motor part and the blower head, a motor atrium is arranged through which the drive shaft of the motor runs.

In some embodiments, the ventilator is characterized in that at least one pressure region with a pressure is present in the blower head and at least one pressure region with a pressure is present in the motor atrium, wherein the pressure in the motor atrium is equal to the pressure in the blower head.

In some embodiments, the ventilator is characterized in that at least one pressure region with a pressure is present in the blower head and at least one pressure region with a pressure is present in the motor atrium, wherein the pressure in the motor atrium is greater than the pressure in the blower head.

In some embodiments, the ventilator is characterized in that the pressure in the motor atrium is constant or is adapted dynamically to the pressure in the blower head.

In some embodiments, the ventilator is characterized in that the pressure in the motor atrium is generated by application of the pressure and/or by a further flow.

In some embodiments, the ventilator is characterized in that the blower comprises at least one feed line, wherein a fluid, in particular a respiratory gas or a respiratory gas mixture, is routed through the feed line into the motor atrium.

In some embodiments, the ventilator is characterized in that a passage is configured and arranged between the motor atrium and the blower head, wherein the drive shaft leads from the motor through the motor atrium and the passage to the fan wheel.

In some embodiments, the ventilator is characterized in that the motor atrium is connected to the blower head in a substantially airtight manner, wherein only the passage permits a leakage between the motor atrium and the blower head.

In some embodiments, the ventilator is characterized in that the blower comprises a suction nozzle with the inlet opening and a pressure nozzle with the outlet opening, wherein the air flow is generated in the blower head and flows from the inlet opening to the outlet opening, and in that the different pressure regions are formed in such a way that at least one additional flow is generated in the blower, wherein the additional flow flows from the motor atrium through the passage into the blower head.

In some embodiments, the ventilator is characterized in that the air flow which flows from an inlet opening to an outlet opening is generated in the blower head and that an additional flow is generated.

In some embodiments, the ventilator is characterized in that the pressure in the motor atrium is greater than the pressure in the blower head, such that the flow flows through the passage from the motor atrium into the blower head.

In some embodiments, the ventilator is characterized in that the motor atrium is formed, by the additional flow, as a clean-room lock, wherein entry of microbes from the blower head into the motor atrium is prevented.

In some embodiments, the ventilator is characterized in that the motor atrium is formed, by the additional flow, as a clean-room lock, wherein entry of microbes from the blower head into the motor is prevented.

In some embodiments, the ventilator is characterized in that the motor is operated free of microbes by the additional flow.

In some embodiments, the ventilator is characterized in that the pressure P2 is applied to the motor atrium via the feed line.

In some embodiments, the ventilator is characterized in that the blower comprises at least one discharge line, wherein a fluid, in particular a respiratory gas or a respiratory gas mixture, is removed from the motor atrium through the discharge line, wherein the discharge line is arranged on the motor atrium and/or on the motor part.

In some embodiments, the ventilator is characterized in that the pressure P2 is applied to the motor atrium via the further flow, wherein the feed line and the discharge line are configured and designed to generate the further flow, by means of a fluid being fed into the motor atrium via the feed line and discharged from the motor atrium via the discharge line.

In some embodiments, the ventilator is characterized in that the feed line is arranged on the motor atrium and/or on the motor part.

In some embodiments, the ventilator is characterized in that the feed line is arranged on the motor atrium, and the pressure is applied to the motor atrium via the feed line.

In some embodiments, the ventilator is characterized in that the feed line is arranged on the motor part, wherein the motor part has at least one channel to which the feed line is coupled in an airtight manner, and wherein the channel opens out in the motor atrium.

In some embodiments, the ventilator is characterized in that the pressure is applied to the motor atrium via the feed line and the channel, and/or the pressure is generated by the further flow.

In some embodiments, the ventilator is characterized in that the motor atrium comprises a discharge line, and the further flow flows from the feed line through the channel into the motor atrium and from there through the discharge line.

In some embodiments, the ventilator is characterized in that the further flow is routed through the at least one channel in such a way that the further flow cools the motor.

In some embodiments, the ventilator is characterized in that the blower is in one piece or two pieces.

In some embodiments, the ventilator is characterized in that the motor atrium is configured and designed to permit a separation of blower head and motor part.

The invention further provides a blower for the above-described ventilator.

The invention also provides a method for operating a ventilator having at least one motor-operated blower for generating an air flow. According to the invention, the method is characterized in that, during the generation of the air flow in the blower, different pressure regions with different pressures are formed in such a way that an air flow in the direction of the motor is prevented.

BRIEF DESCRIPTION OF THE DRAWINGS

Illustrative embodiments of the ventilator according to the invention are depicted in the drawings, in which.

DETAILED DESCRIPTION OF EXEMPLARY EMBODIMENTS

Figure 1:
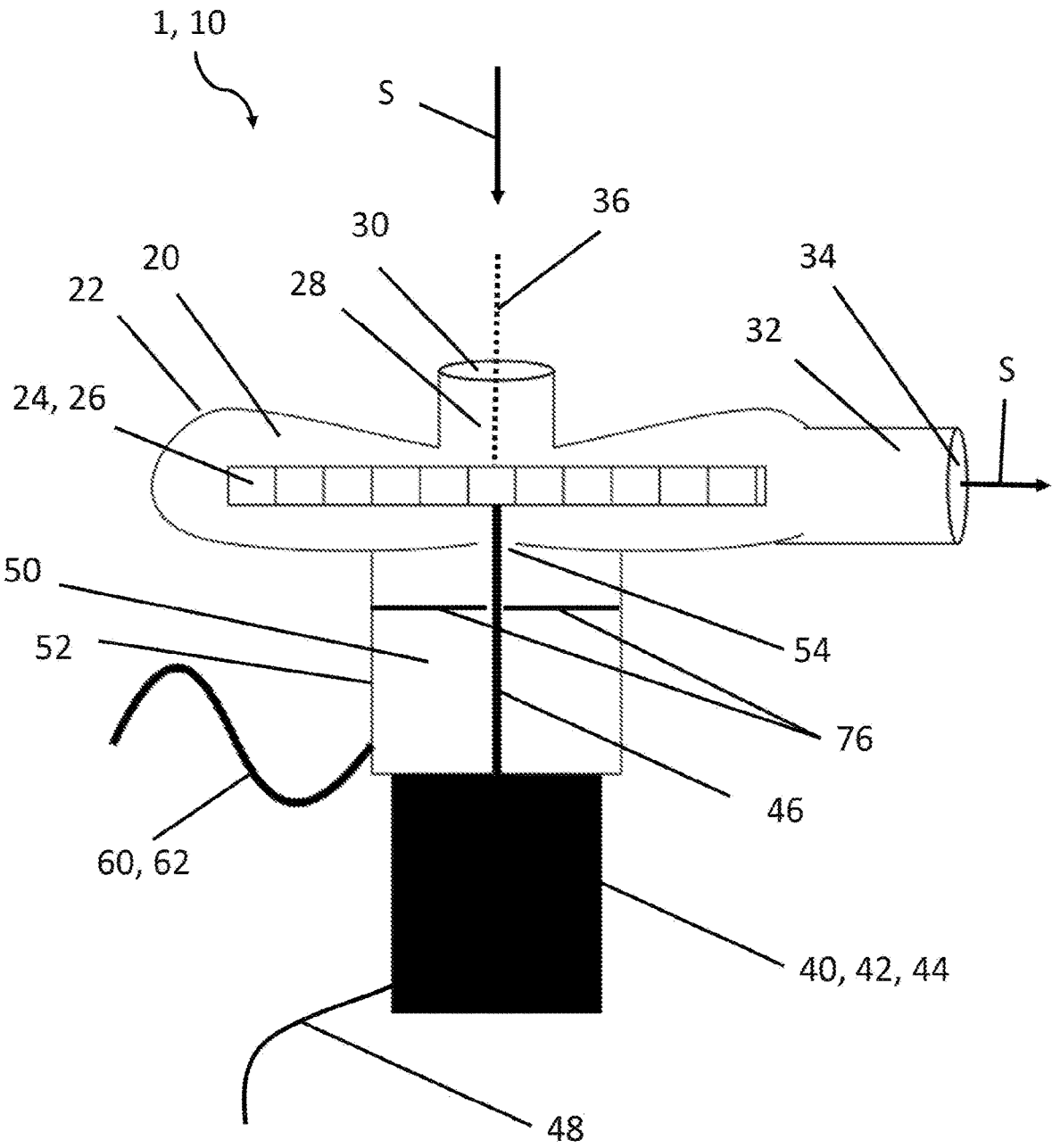
FIG. 1 shows, in cross section, a schematic detail of a ventilator according to the invention having a blower according to the invention.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

A ventilator in the context of the invention is understood to cover all appliances which assist the natural breathing of a patient or other user and/or which take over the ventilation of a user or patient and/or which serve for respiratory therapy and/or which act in some other way on the respiration of a user or patient. These include by way of example, but not exclusively, ventilators for use in hospitals or at home, respiration therapy appliances, CPAP, APAP and Bi-Level appliances, high-flow therapy appliances, anesthesia appliances, ventilators for use in hospitals, in non-hospital environments or in emergencies, appliances supplying oxygen $O_2$, diagnostic systems, and cough therapy appliances or coughing machines.

The ventilator 1 is equipped with a blower 10 according to the invention, which is accommodated in the appliance interior and comprises at least one fan wheel 24 with which an air flow S for ventilation or respiratory therapy is generated. In particular, an exhalation air flow S for ventilation or respiratory therapy is generated. Respiratory air within the context of the invention comprises any fluid, respiratory gas and/or gas mixture which is suitable and can be used for ventilation, respiration and/or respiratory therapy. Respiratory air and fresh gas are used herein as synonyms. The respiratory air or the fresh gas can also be oxygen or oxygen-enriched air. In particular, the respiratory air or the fresh gas can also contain at least one anesthetic gas and be suitable for anesthesia appliances.

The blower 10 is controlled via a control device arranged in the appliance interior. For example, the control device sets a defined speed of rotation of the fan wheel 24, or regulates the fan speed to a setpoint value, according to the therapy goals.

Ventilator 1 has an interface for coupling a hose system, via which a (respiratory) air flow S can be fed to the patient or user for ventilation, respiratory assistance or cough assistance. For this purpose, a patient interface can be attached to the hose system. In the context of the invention, a patient interface can be understood as any peripheral designed for interaction with a living being. In particular, the patient interface is designed for therapeutic and/or diagnostic purposes in conjunction with the ventilator 1. The patient interface can be designed as a breathing mask. This includes, for example but not exclusively, nose masks, padded nose masks, nasal cannulas, full-face masks and also tracheal tubes or cannulas.

FIG. 1 shows, in cross section, a schematic detail of a ventilator 1 according to the invention having a blower 10 according to the invention. The blower 10 of the ventilator 1 comprises a blower head 20, a motor part 40 and a motor atrium 50.

Motor part 40 has a motor housing 42. A drive device or a motor 44 having an electrical drive is mounted in the motor housing 42. To operate motor 44, motor part 40 can have an electrical connection 48 which can supply the motor 44 with energy. The motor 44 is connected to a drive shaft 46, which can be brought into rotation via the motor 44. The drive shaft 46 can be in one piece or in two pieces. Motor 44 can be controlled via a control device of the ventilator 1, such that defined speeds of rotation can be dynamically adjusted.

Blower head 20 has a fan wheel housing 22, in which at least one fan wheel 24 is arranged. The fan wheel 24 comprises a plurality of blade elements 26. To rotate the fan wheel 24, the blower 10 has, in motor part 40, motor 44 with an electrical drive. Motor 44 can transmit rotational energy to the fan wheel 24 via the drive shaft 46. The rotational movement creates a pressure side and a vacuum side at the fan wheel 24, which results in the (respiratory) air flow S with a flow direction. The flow direction is indicated in the figures by arrows. The air flow S runs substantially from an inlet opening 30 to an outlet opening 34 of blower 1. The control device of ventilator 1 is configured and designed to dynamically control the fan wheel 24 and operate it at high rotational speeds of up to 100,000 rpm.

The fan wheel housing 22 of the blower head 20 generally has a spiral shape. Blower 10 comprises a suction nozzle 28 with the inlet opening 30. Suction nozzle 28 has a central axis 36. Blowers 10 used in ventilators 1 are usually radial blowers. In radial blowers, a fluid, for example respiratory air, enters the blower head 20 in the axial direction and leaves the blower 10 perpendicular to the axial direction. In addition to respiratory air, blower 10 can also transport any other gas mixture that is needed for respiratory therapy. The fluid, for example respiratory air, can be sucked in via the suction nozzle 28. The respiratory air passes through the suction nozzle 28 in the axial direction into the blower head 20. Blower 10 further comprises a pressure nozzle 32 with the outlet opening 34. The fluid can be dispensed via the pressure nozzle. The respiratory air exits the blower head 20 through the pressure nozzle 32 perpendicular to the axial direction. The spiral-shaped fan wheel housing 22 ensures that the respiratory air is collected in the blower head 20 and routed to the pressure nozzle 32, where it exits the blower head 20. This prevents the creation of circling outlet flows, which lead to losses. At the same time, some of the speed energy of the respiratory air is converted into pressure energy by the spiral housing 10.

Hose connections (not shown) can be attached to the suction nozzle 28 and/or the pressure nozzle 32. By way of a hose connection at the suction nozzle 28, for example, fresh gas can be passed into the fan wheel housing 22. By way of a hose connection at pressure nozzle 32, the fresh gas can be fed to the patient.

Suction nozzle 28 and/or pressure nozzle 32 can additionally be used to clean and/or disinfect the blower. The cleaning and/or disinfection can be carried out, for example, by the blower 1 being placed in a cleaning or disinfecting device. A cleaning liquid can then be introduced into the fan wheel housing 24 via the pressure nozzle 32 and/or the suction nozzle 28. Here, a cleaning liquid denotes any agent suitable for cleaning and/or disinfecting the blower 1. Cleaning and disinfecting are used synonymously here. Cleaning can include disinfecting, and disinfecting can include cleaning.

For example, hose connections which connect the blower 1 to the cleaning or disinfecting device can be attached to the pressure nozzle 32 and/or the suction nozzle. The cleaning liquid can be introduced with at least about 50 mbar, preferably with at least about 80 mbar, particularly preferably with at least about 100 mbar into the fan wheel housing 22. The pressure with which the cleaning liquid is introduced should be chosen sufficiently high that the cleaning liquid has the possibility of reaching all regions inside the blower head 20. At the same time, the chosen pressure should be sufficiently low that blower 1 is not damaged.

Chemically aggressive cleaning liquids are generally used for cleaning or disinfecting. These may cause damage particularly in the motor part 20, for example wear and tear at bearings, a negative impact on adhesives at bonded points within motor part 20, and/or contact corrosion. For these reasons, it is advantageous if motor part 20 can be excluded from the cleaning/disinfecting or if contact between the cleaning or disinfecting agent and motor part 40 can be prevented as far as possible or can at least be reduced.

For this purpose, blower 1 according to the invention has a motor atrium 50. The motor atrium 50 affords many advantages. Firstly, motor atrium 50 is configured and designed to prevent contamination of motor part 40. Secondly, by means of motor atrium 50, cleaning and/or disinfecting agent can be prevented from reaching motor part 40. The stated advantages are described in greater detail below.

The motor atrium 50 has an atrium housing 52. The atrium housing 52 can be in one piece (see FIGS. 1-3) or in two pieces (see FIG. 4).

The atrium housing 52 is arranged between blower head 20 and motor part 40. The atrium housing 52 encloses the interior of the motor atrium 50. On the one hand, the atrium housing 52 is connected to the fan wheel housing 22 in a substantially airtight manner. On the other hand, atrium housing 52 is connected to motor housing 42 in a substantially airtight manner. Drive shaft 46 leads from motor part 40 through atrium housing 52 into the blower head 20. In blower head 20, the drive shaft 46 is connected to the fan wheel 24.

A passage 54 through which the drive shaft 46 of the motor 44 runs is configured and designed between the motor atrium 50 and the blower head 20. Passage 54 can be sealed mechanically. Passage 54 is preferably not sealed mechanically, so as to avoid frictional losses and to obtain particularly high speeds of the fan wheel 24. Passage 54 can permit leakage between blower head 20 and motor atrium 50.

Blower 10 according to the invention can comprise at least one feed line 60. The motor atrium 50 can be filled with a fluid via the feed line 60. A pressure P can be applied to the motor atrium 50 via the feed line 60. By way of the feed line 60, a flow can also be generated in the motor atrium 50, which flow generates a pressure P in the motor atrium 50.

Fresh gas is preferably introduced into the motor atrium 50. Fresh gas can be routed through feed line 60 into the atrium housing 52, such that the motor atrium 50 can be brought to an overpressure in relation to the blower head 20. The overpressure in the motor atrium 50 can for example be maintained statically at one pressure level. In some embodiments, the overpressure in the motor atrium 50 can also be adapted dynamically to the pressure delivered by the blower 1. For this purpose, one or more feed valves 62 can be arranged in the feed line 60. The feed valves 62 can for example constitute a stage system, wherein different pressure stages can be offered by the feed valves 62. Alternatively or in addition, a second blower 1' can also be provided, which can make available a static and/or dynamically adapted pressure P and/or flow for the feed line 60.

Figure 2:
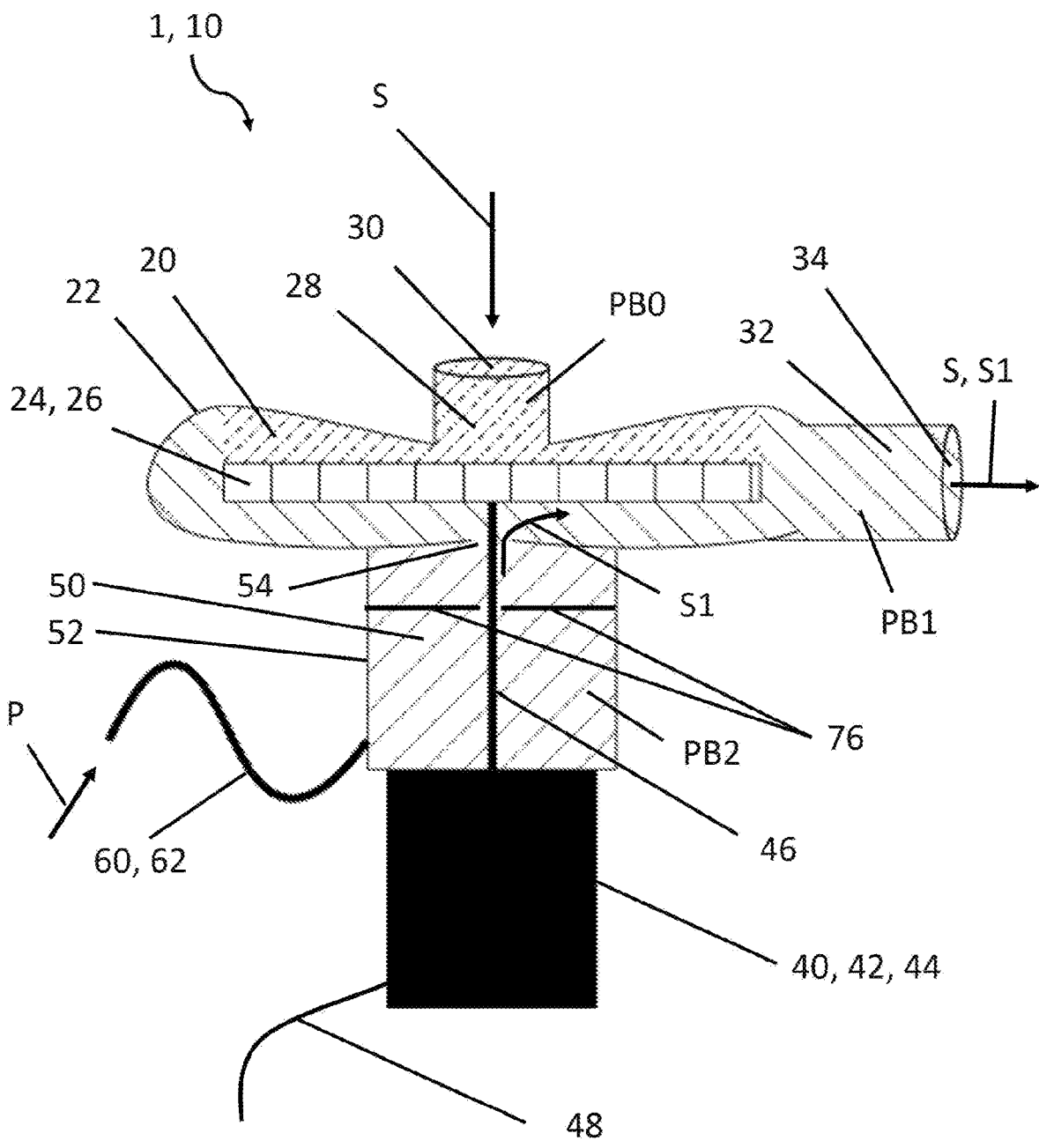
FIG. 2 shows, in cross section, a schematic detail of the ventilator according to the invention having the blower according to the invention, illustrating various flows and different pressure regions.

In the illustrative embodiment according to FIG. 1/FIG. 2, the feed line 60 can be arranged on the atrium housing 52. The atrium housing 52 for this purpose has an opening to which the feed line 60 can be coupled in an airtight manner. By way of feed line 60, the fresh gas for generating the overpressure can be introduced directly into the motor atrium 50.

The feed line 60 can be arranged at any location of the atrium housing 52 that appears to be suitable. Preferably, feed line 60 is arranged adjacent to motor part 40. For example, feed line 60 is arranged in the region of the atrium housing 52 that is farthest away from the blower head 20.

FIG. 2 shows, in cross section, a schematic detail of the ventilator 1 according to the invention having the blower 10 according to the invention, illustrating various flows S, S1 and different pressure regions PB0, PB1, PB2.

The pressure conditions inside the blower 1 are shown schematically and in simplified form in FIG. 2. Different regions inside the blower 1, in each of which regions there is substantially the same pressure P, are depicted with different hatching. During operation of the blower 1, there may be basically three pressure regions PB0, PB1 and PB2.

In the suction nozzle 28 and in the region upstream from the fan wheel 24, there may be a pressure region PB0, in which there is a pressure P0.

Downstream from the fan wheel 24 in the direction of flow, toward the outlet opening 34 and in the pressure nozzle 32, there can be a pressure region PB1 with an elevated pressure P1 generated by the fan wheel 24. Accordingly, the pressure P1 is also present downstream from the fan wheel 24 in the region of passage 54. During operation of the blower 1, the pressure P1 is greater than the pressure P0.

In motor atrium 50, there can be a pressure region PB2 in which there is a pressure P2. The pressure region PB2 in the motor atrium 50 is brought to the pressure P2 via the feed line 60. Preferably, the pressure P2 is greater than the pressure P1. By virtue of the fact that the pressure P2 is greater than the pressure P1, admission of the respiratory air charged with microbes during operation is prevented. Accordingly, the following preferably applies in the blower 1: P2>P1>P0. In particular, P2>P1>P0 applies during the operation of the blower 1.

The overpressure in the motor atrium 50 can preferably give rise to a small and constant air flow, an additional flow S1, from the motor atrium 50 into the blower head 20.

The additional flow S1 prevents microbes from entering the motor atrium 50. In particular, the additional flow S1 prevents a situation where microbes from the patient's respiratory air, which enters the blower head 20 in a semi-closed circuit, reach their way from the blower head 20 into the motor atrium 50. The motor atrium 50 can thus be configured and designed as a clean-room lock which, within the meaning of the invention, signifies that the motor atrium 50 is at least almost free of microbes and preferably completely free of microbes. By virtue of the motor atrium being almost free of microbes or completely free of microbes, the motor part 40 can also be operated in a manner almost free of microbes or completely free of microbes.

Within the meaning of the invention, microbes comprise all airborne particles that are undesirable in the blower 1 and that may have adverse effects on patients. Microbes comprise in particular microorganisms such as fungi, bacteria, algae, parasites, prions, protists, viruses or viroids and derivatives thereof or precursors such as fungal spores, spores, allergens, toxins and the like. Microbes can in particular be understood as pathogens.

In this embodiment, the pressure P2 is preferably maintained at a constant, static pressure. The additional flow S1 arises as a result of the illustrated pressure conditions of P0, P1 and P2 and the passage 54 arranged between the fan wheel housing 22 and the atrium housing 52. The flow S1 flows from the atrium housing 52 through passage 54 into the fan wheel housing 22. In the fan wheel housing 22, the flow S1 can combine with the air flow S and be conveyed to the outlet opening 34.

Fresh gas, which may also be intended for the patient, is preferably introduced through the feed line 60 into the motor atrium 52. By virtue of the fact that fresh gas is used to produce the overpressure in the motor atrium 50, some of the necessary gas input for replenishing the respiratory air for the patient can be provided through the intentional leakage in the passage 54.

The additional air flow S1 prevents microbes from being able to pass from the blower head 20 into the motor atrium 50. The additional air flow S1 also prevents microbes from being able to reach the motor part 40. The motor part 40 and/or the motor atrium 50 can therefore be excluded from cleaning and/or disinfecting after the blower 1 has been operated with a clean-room lock in the motor atrium 50.

For cleaning and/or disinfecting, the blower 1 can for example be placed into a cleaning or disinfecting appliance with the motor part 40 facing upward and with the blower head 20 facing downward. Then, by way of the pressure nozzle 32 and/or the suction nozzle 28, a cleaning liquid can be introduced into the fan wheel housing 22 and can preferably fill the latter. Gravity keeps the cleaning liquid for the most part in the blower head 20 at the bottom. Potentially, however, cleaning liquid may undesirably pass through the passage 54 into the motor atrium 50. To ensure that the cleaning liquid cannot reach the motor part 40 and cause damage there, the motor atrium 50 is arranged between the blower head 20 and the motor part 40. In addition, the motor atrium 50 can contain special protective mechanisms which are configured and designed to keep the cleaning liquid away from the motor part.

In some embodiments, for example, one or more baffle elements 76 can be arranged in the atrium housing 52 (see FIG. 1/FIG. 2). The baffle elements 76 are configured and designed to keep encroaching cleaning liquid in the form of spray water away from the motor part 40. The baffle elements 76 can be designed, for example, in the form of one or more panels which divide the atrium housing into two portions and leave only a very small space free in the region of the drive shaft 46.

In some embodiments, one or more outflow openings (not shown) can alternatively or additionally be arranged in the atrium housing 52. During the operation of the blower 1, the outflow openings can be closed in an airtight manner. For a cleaning and/or disinfecting process, by contrast, the outflow openings can be opened, such that any incoming cleaning liquid can be discharged from the motor atrium 59 before reaching the motor part 40. In some illustrative embodiments, baffle elements 76, additionally arranged for this purpose, can advantageously be configured and designed to lead the incoming cleaning liquid to the outflow openings of the motor atrium 50.

In alternative embodiments, the atrium housing 52 can alternatively or additionally have a special shape (not shown) that is able to keep any encroaching cleaning liquid away from the motor part 20. For example, the atrium housing 52 can have one or more constrictions, such that one or more narrowed locations are obtained which are able to keep the spray water of the cleaning liquid away from the motor part 40. In an illustrative embodiment, the motor atrium 50 can have an hourglass shape.

Figure 3:
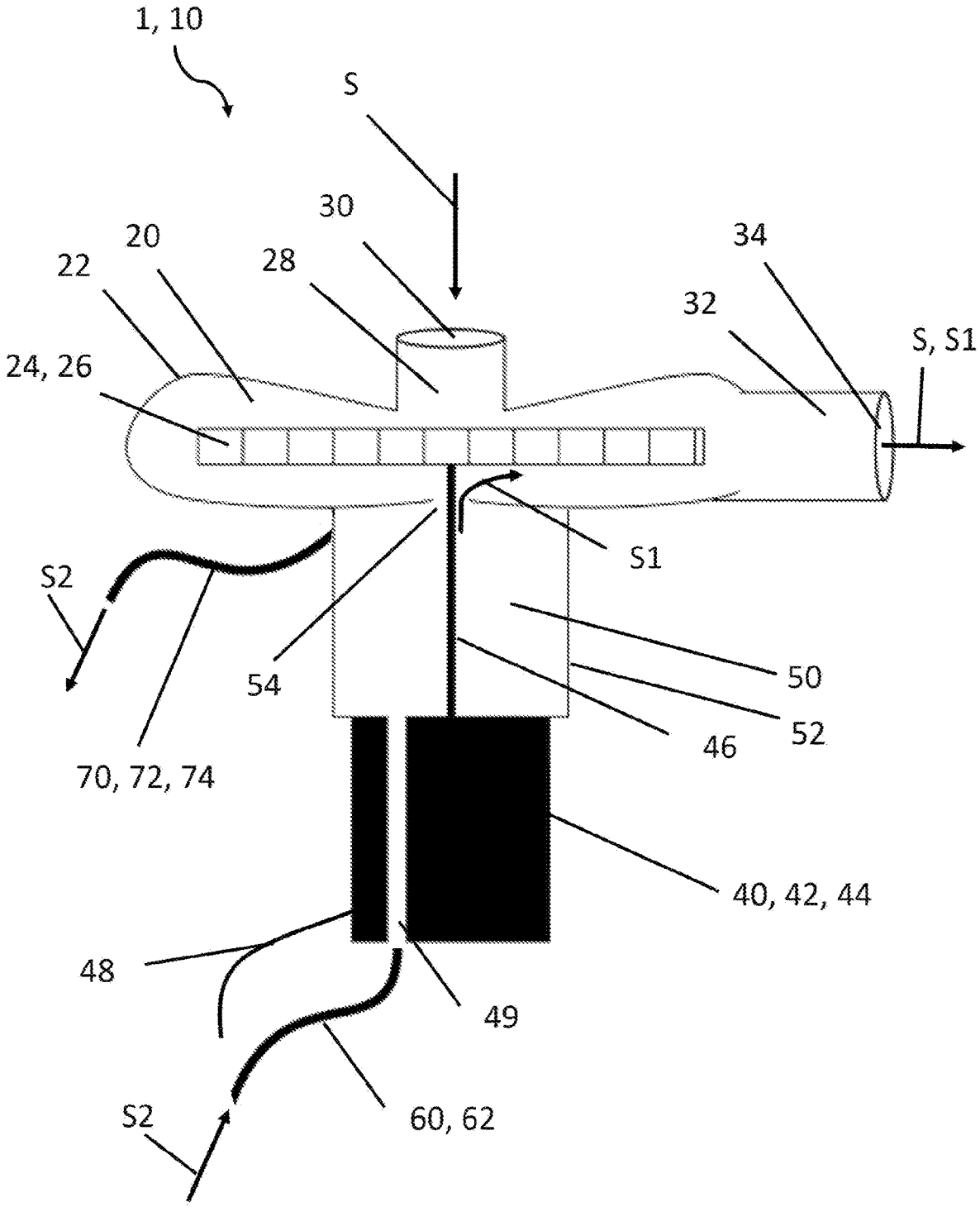
FIG. 3 shows, in cross section, a schematic detail of an alternative illustrative embodiment of the ventilator according to the invention having a blower according to the invention.

FIG. 3 shows, in cross section, a schematic detail of an alternative illustrative embodiment of the ventilator 1 according to the invention having a blower 10 according to the invention.

FIG. 3 shows that the feed line 60 can also be arranged on the motor part 40. For this purpose, the motor part 4 has an opening to which the feed line 60 can be coupled in an airtight manner. The opening is designed for example as at least one channel 49. The at least one channel 49 connects the feed line 60 to the interior of the atrium housing 52. It is also possible to provide a plurality of feed lines 60 and/or a plurality of channels 49 through the motor part 40. By way of the feed line 60, fresh gas can introduced through the channel 49 into the atrium housing 52.

The fresh gas can be used, in accordance with the previously described illustrative embodiment, to generate a constant pressure in the atrium housing 52.

In this illustrative embodiment, the fresh gas introduced into the atrium housing 52 via the channel 49 can preferably also be used to generate a further flow S2. For this purpose, the blower 1 can comprise a discharge line 70 is some embodiments. The discharge line 70 can moreover have one or more discharge valves 72 and/or throttle elements 74.

The discharge line 70 is, for example, configured and designed to lead the flow S2 in a constant manner through the at least one channel 49 and the atrium housing 52. The flow S2 can also be adapted dynamically to the (respiratory) air flow S generated in the blower head 20. The discharge valves 72 and/or throttle elements 74 in the discharge line 70 can be configured in such a way that the pressure P2 in the motor atrium 50 is always above the pressure P1 in the blower head 20. Thus, the pressure P2 can be adapted dynamically to the pressure conditions in the blower head 20.

In one illustrative embodiment, the channel 49 can run lengthwise straight through the motor part 40 (see FIG. 3). In some embodiments, it is possible that the channel 49 covers the greatest possible distance in the motor part 40. For example, the channel 49 can run in a loop shape through the motor part 40 and/or can have one or more branches. In some embodiments, it is also conceivable that a plurality of channels 49 extend through the motor part 40 (not shown).

The one or more channels 49 have the additional advantage that the motor part 40 or the motor 44 can be cooled by the air flow of the fresh gas. Cooling of the motor 44 is usually necessary during operation. Additional cooling devices for the motor 44 can be rendered obsolete by the design of the channels 49. At the same time, the passage of the fresh gas through the motor part 40 has the advantage that the fresh gas can be warmed. Warmed fresh gas may be advantageous and/or necessary for respiratory therapy and/or ventilation.

The flow S2 can flow largely from the feed line 60 through channel 49 into the atrium housing 52. From the atrium housing 52, the flow S2 can be largely discharged through the discharge line 70.

An overpressure can be generated in the motor atrium 50 by the flow S2. The overpressure in the motor atrium in turn gives rise to the additional flow S1, which flows from the motor atrium 50 into the blower head 20. The flow S1, which results from the overpressure in the motor atrium 50, flows through passage 54 into the fan wheel housing 22. In the fan wheel housing 22, the flow S1 can combine with the air flow S and be conveyed to the outlet opening 34.

The flow S2, which is discharged through the discharge line 70, can advantageously remain in the semi-closed circuit. For example, the flow S2 discharged through the discharge line 70 can then be fed back to the feed line 60. Alternatively or in addition, the flow S2 discharged through the discharge line 70 can also be introduced via the suction nozzle 28 into the blower head 20, where it can be made available for generating the (respiratory) air flow S.

Figure 4:
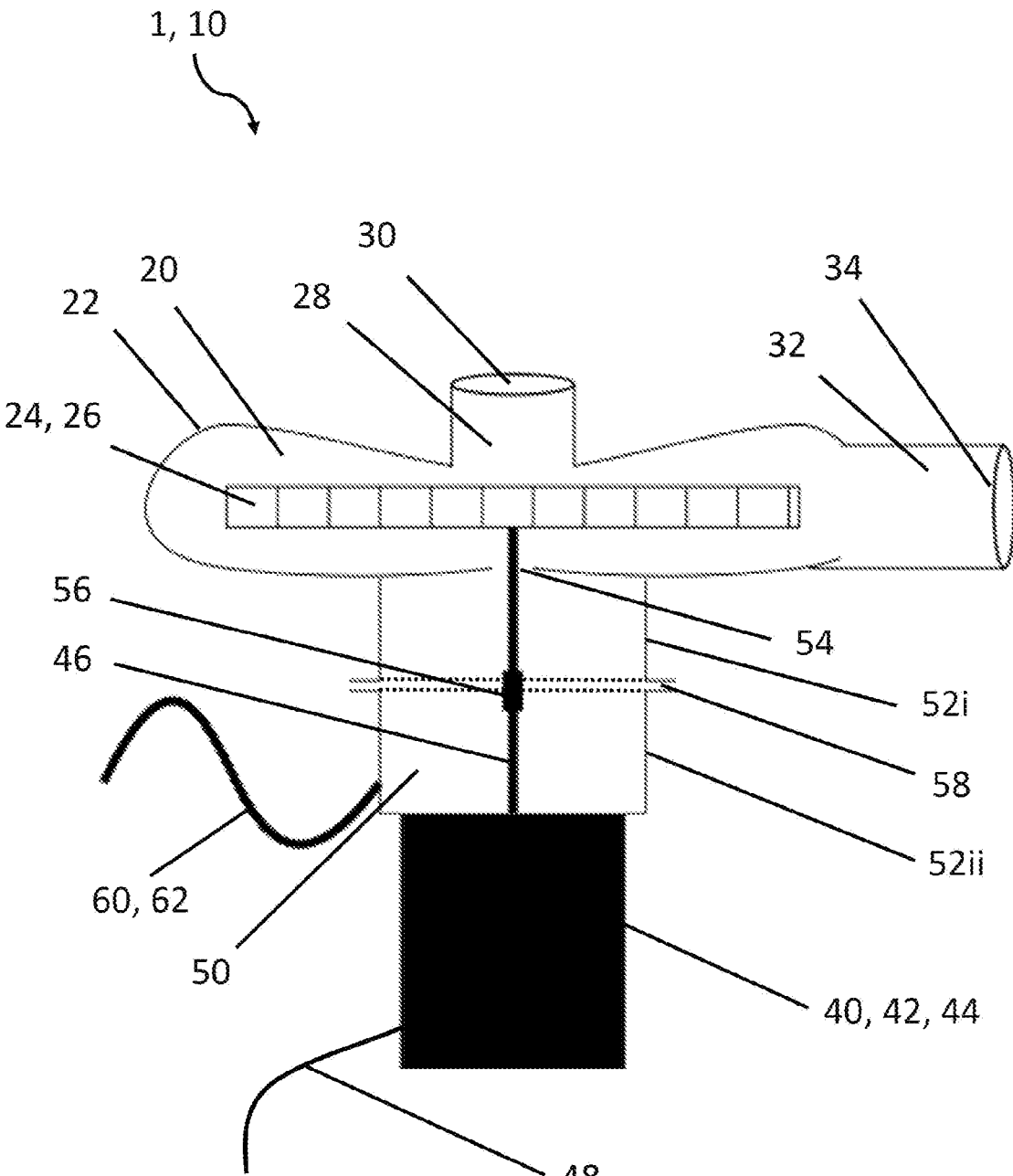
FIG. 4 shows, in cross section, a schematic detail of a further illustrative embodiment of the ventilator according to the invention having a blower according to the invention

FIG. 4 shows, in cross section, a schematic detail of a further illustrative embodiment of the ventilator 1 according to the invention having a blower 10 according to the invention. FIG. 4 shows that, in some embodiments, the motor atrium 50 can be configured and designed in such a way that a separation of blower head 20 and motor 40 is possible.

In some embodiments, the motor atrium 50 can be coupled releasably (not shown) to the blower head 20 and/or to the motor part 40. In an advantageous embodiment, the atrium housing 52 can also be in two pieces (see FIG. 4). A two-piece atrium housing 52 can comprise two atrium housing parts 52i and 52ii and a housing coupling 58.

The atrium housing parts 52i, 52ii can be coupled to each other via the housing coupling 58 with form-fit and/or force-fit engagement. Preferably, the atrium housing parts 52i, 52ii are coupled to each other in an airtight manner. When the atrium housing parts 52i, 52ii are coupled to each other in an airtight manner, the blower 1 can be put into operation and a (respiratory) air flow can be generated.

The coupling can be reversible or irreversible. The coupling is preferably reversible. A reversible coupling of the atrium housing parts 52i, 52ii affords the advantage that the blower 1 can be separated. Separation of the blower 1 may be advantageous, for example, for cleaning or disinfecting and/or for other treatments and/or for maintenance or repair purposes.

For the purpose of separating the blower 1, the drive shaft 46 can likewise be designed in two pieces and comprise an axial coupling 47. During operation, the drive shaft 46 can be connected via the axial coupling 47 with form-fit and/or force-fit engagement. To separate the blower 1, the axial coupling 47 can be released. The axial coupling 47 can be arranged at any region within drive shaft 46. In this specific illustrative embodiment according to FIG. 4, the axial coupling 47 is arranged in that region of the drive shaft 46 located in the motor atrium 50.

For example, blower 1 can be separated in preparation for cleaning and/or disinfecting. In this way, it is possible to dispense with treating motor part 20, since the motor part 20, as has been described above, was not exposed to contamination during operation. Thus, motor part 20 can be protected against damage caused by a cleaning process. When blower 1 is separated, it is then possible to clean or disinfect only the contaminated region, namely the blower head 20 and/or the motor atrium 50.

To sum up, the present invention provides:

1. A ventilator which comprises at least one motor-operated blower for generating an air flow S, the blower being configured and designed such that during generation of air flow S in the blower different pressure regions PB with different pressures P are formed in such a way that an air flow S in a direction of the motor is prevented.

2. The ventilator of item 1, wherein the blower comprises at least one motor part with the motor and a drive shaft and also a blower head having a rotatably mounted fan wheel, and wherein, between the motor part and the blower head, a motor atrium is arranged through which the drive shaft of the motor runs.

3. The ventilator of any one of the preceding items, wherein at least one pressure region PB1 with a pressure P1 is present in the blower head and at least one pressure region PB2 with a pressure P2 is present in the motor atrium, the pressure P2 in the motor atrium being equal to or greater than the pressure P1 in the blower head.

4. The ventilator of any one of the preceding items, wherein the pressure P2 in the motor atrium is constant or is adapted dynamically to the pressure P1 in the blower head.

5. The ventilator of any one of the preceding items, wherein the pressure P2 in the motor atrium is generated by application of the pressure P2 and/or by a further flow S2.

6. The ventilator of any one of the preceding items, wherein the blower comprises at least one feed line in which a fluid, in particular a respiratory gas or a respiratory gas mixture, is routed through the feed line into the motor atrium, the feed line being arranged on the motor atrium and/or on the motor part.

7. The ventilator of any one of the preceding items, wherein a passage is configured and arranged between the motor atrium and the blower head, the drive shaft leading from the motor through the motor atrium and the passage to the fan wheel in the blower head.

8. The ventilator of any one of the preceding items, wherein the motor atrium is connected to the blower head in a substantially airtight manner, only the passage permitting a leakage between the motor atrium and the blower head.

9. The ventilator of any one of the preceding items, wherein the blower further comprises a suction nozzle with an inlet opening and a pressure nozzle with an outlet opening, and wherein the air flow S is generated in the blower head and flows from the inlet opening to the outlet opening, different pressure regions PB1 and PB2 being formed in such a way that at least one additional flow S1 is generated in the blower, the additional flow S1 flowing from the motor atrium through the passage into the blower head.

10. The ventilator of any one of the preceding items, wherein the motor atrium is formed, by the additional flow S1, as a clean-room lock, in which entry of microbes from the blower head into the motor atrium and/or the motor is prevented, such that the motor is operated free of microbes by the additional flow S1.

11. The ventilator of any one of the preceding items, wherein pressure P2 is applied to the motor atrium via the feed line.

12. The ventilator of any one of the preceding items, wherein the blower further comprises at least one discharge line, and wherein a fluid, in particular a respiratory gas or a respiratory gas mixture, is removed from the motor atrium through the discharge line, the discharge line being arranged on the motor atrium and/or on the motor part.

13. The ventilator of any one of the preceding items, wherein pressure P2 is applied to the motor atrium via a further flow S2, the feed line and a discharge line being configured and designed to generate the further flow S2, by means of a fluid being fed into the motor atrium via the feed line and discharged from the motor atrium via the discharge line.

14. The ventilator of any one of the preceding items, wherein the feed line is arranged on the motor part, wherein the motor part comprises at least one channel to which the feed line is coupled in an airtight manner, wherein the at least one channel opens out in the motor atrium, and wherein the pressure P2 is applied to the motor atrium via the feed line and the at least one channel, and/or wherein the pressure P2 is generated by the further flow S2.

15. The ventilator of any one of the preceding items, wherein the motor atrium comprises the discharge line, and the further flow S2 flows from the feed line through the at least one channel into the motor atrium and from there through the discharge line.

16. The ventilator of any one of the preceding items, wherein the further flow S2 is routed through the at least one channel in such a way that the further flow S2 cools the motor.

17. The ventilator of any one of the preceding items, wherein the blower is in one piece or in two pieces.

18. The ventilator of any one of the preceding items, wherein the motor atrium is configured and designed to permit a separation of blower head and motor part.

19. A blower, wherein the blower is suitable for use with the ventilator of any one of the preceding items.

20. A method for operating a ventilator comprising at least one motor-operated blower for generating an air flow S, wherein, during the generation of the air flow S in the blower, different pressure regions PB with different pressures P are formed in such a way that an air flow S in the direction of the motor is prevented.

Although the present invention has been described in detail on the basis of the illustrative embodiments, it is self-evident to a person skilled in the art that the invention is not restricted to said illustrative embodiments. On the contrary, modifications involving omission of individual features or realization of different combinations of the described individual features are possible, provided that there is no departure from the scope of protection of the appended claims. The present disclosure includes all combinations of the individual features presented.

LIST OF REFERENCE SIGNS 1 ventilator
10 blower
20 blower head
22 fan wheel housing
24 fan wheel
26 blade elements
28 suction nozzle
30 inlet opening
32 pressure nozzle
34 outlet opening
36 central axis
40 motor part
42 motor housing
44 motor
46 drive shaft
47 axial coupling
48 electrical connection
49 channel
50 motor atrium
52 atrium housing
52i, 52ii atrium housing parts 54 passage
58 housing coupling
60 feed line
62 feed valves
70 discharge
72 discharge valves
74 throttle elements
76 baffle elements
P pressure
PB pressure regions
S (air) flow
S1 additional flow
S2 further flow

What is claimed is:

1. A ventilator, wherein the ventilator comprises at least one motor-operated blower for generating an air flow S in the blower, the blower comprising a blower head comprising a rotatably mounted blower wheel, a motor part comprising a motor and a drive shaft for driving the blower wheel, a motor atrium arranged between the motor part and the blower head, the drive shaft leading from the motor through the motor atrium to the blower wheel through a passage between the motor atrium and the blower head, at least one feed line arranged on the motor atrium and/or the motor part through which a fluid is routed into the motor atrium, the blower being configured such that when the air flow S is generated, a first pressure P1 is formed in at least one first pressure region PB1 in the blower head and a second pressure P2 is formed in at least one second pressure region PB2 in the motor atrium, the second pressure P2 being applied via the at least one feed line and being higher than the first pressure P1 to prevent an air flow in a direction of the motor.

2. The ventilator of claim 1, wherein the second pressure P2 in the motor atrium is constant.

3. The ventilator of claim 1, wherein the second pressure P2 in the motor atrium is adapted dynamically to the first pressure P1 in the blower head.

4. The ventilator of claim 1, wherein the passage between the motor atrium and the blower head permits a leakage of fluid between the motor atrium and the blower head.

5. The ventilator of claim 1, wherein the blower further comprises a suction nozzle with an inlet opening and a pressure nozzle with an outlet opening, and wherein the air flow S is generated in the blower head and flows from the inlet opening to the outlet opening, the at least one pressure region PB1 and the at least one pressure region PB2 being formed in such a way that at least one additional flow S1 is generated in the blower, the additional flow S1 flowing from the motor atrium through the passage into the blower head.

6. The ventilator of claim 5, wherein the motor atrium is formed, by the additional flow S1, as a clean-room lock, in which entry of microbes from the blower head into the motor atrium and/or the motor is prevented, such that the motor is operated free of microbes by the additional flow S1.

7. The ventilator of claim 1, wherein the at least one feed line is arranged on the motor atrium.

8. The ventilator of claim 1, wherein the at least one feed line is arranged on the motor part.

9. The ventilator of claim 1, wherein the blower further comprises at least one discharge line, and wherein a fluid is removed from the motor atrium through the at least one discharge line, the at least one discharge line being arranged on the motor atrium and/or on the motor part.

10. The ventilator of claim 1, wherein the second pressure P2 is applied to the motor atrium via a further flow S2, the at least one feed line and a discharge line being configured and designed to generate the further flow S2, by means of a fluid being fed into the motor atrium via the at least one feed line and discharged from the motor atrium via the discharge line.

11. The ventilator of claim 10, wherein the at least one feed line is arranged on the motor part, wherein the motor part comprises at least one channel to which the at least one feed line is coupled in an airtight manner, wherein the at least one channel opens out in the motor atrium, and wherein the second pressure P2 is applied to the motor atrium via the at least one feed line and the at least one channel, and/or wherein the second pressure P2 is generated by the further flow S2.

12. The ventilator of claim 11, wherein the motor atrium comprises the discharge line, and the further flow S2 flows from the at least one feed line through the at least one channel into the motor atrium and from there through the discharge line.

13. The ventilator of claim 11, wherein the further flow S2 is routed through the at least one channel in such a way that the further flow S2 cools the motor.

14. The ventilator of claim 1, wherein the blower is present as one part.

15. The ventilator of claim 1, wherein the blower is present as two parts.

16. The ventilator of claim 1, wherein the motor atrium is configured and designed to permit a separation of blower head and motor part.

17. A blower for generating an airflow S in the blower, wherein the blower is suitable for use with a ventilator, is motor-operated and comprises a blower head comprising a rotatably mounted blower wheel, a motor part comprising a motor and a drive shaft for driving the blower wheel, a motor atrium arranged between the motor part and the blower head, the drive shaft leading from the motor through the motor atrium to the blower wheel through a passage between the motor atrium and the blower head, at least one feed line arranged on the motor atrium and/or the motor part through which a fluid is routed into the motor atrium, the blower being configured such that when the air flow S is generated, a first pressure P1 is formed in at least one first pressure region PB1 in the blower head and a second pressure P2 is formed in at least one second pressure region PB2 in the motor atrium, the second pressure P2 being applied via the at least one feed line and being higher than the first pressure P1 to prevent an air flow in a direction of the motor.

18. A method of preventing contamination in a motor-operated blower of a ventilator, wherein the blower comprises a blower head comprising a rotatably mounted blower wheel, a motor part comprising a motor and a drive shaft for driving the blower wheel, a motor atrium arranged between the motor part and the blower head, the drive shaft leading from the motor through the motor atrium to the blower wheel through a passage between the motor atrium and the blower head, at least one feed line arranged on the motor atrium and/or the motor part through which a fluid is routed into the motor atrium, and wherein the method comprises generating an air flow S in the blower head, forming a first pressure P1 in at least one first pressure region PB1 in the blower head and forming a second pressure P2 in at least one second pressure region PB2 in the motor atrium, and applying the second pressure P2 via the at least one feed line and causing it to be higher than the first pressure P1 to prevent an air flow in a direction of the motor.

* * * * *